(12) United States Patent
Mersmann et al.

(10) Patent No.: US 9,802,016 B2
(45) Date of Patent: Oct. 31, 2017

(54) RESPIRATION SYSTEM

(71) Applicant: DRÄGER MEDICAL GMBH, Lübeck (DE)

(72) Inventors: Stefan Mersmann, Lübeck (DE); Thomas Katschewitz, Lübeck (DE); Andreas Neumann, Klempau (DE); Philippe Jolliet, Lausanne (CH)

(73) Assignee: Drägerwerk AG & Co. KGaA, Lübeck (DE)

( * ) Notice: Subject to any disclaimer, the term of this patent is extended or adjusted under 35 U.S.C. 154(b) by 601 days.

(21) Appl. No.: 14/377,700

(22) PCT Filed: Jan. 29, 2013

(86) PCT No.: PCT/EP2013/051666
§ 371 (c)(1),
(2) Date: Aug. 8, 2014

(87) PCT Pub. No.: WO2013/120690
PCT Pub. Date: Aug. 22, 2013

(65) Prior Publication Data
US 2015/0335839 A1 Nov. 26, 2015

(30) Foreign Application Priority Data
Feb. 16, 2012 (DE) .......................... 10 2012 003 115

(51) Int. Cl.
*A61M 16/00* (2006.01)
*A61B 5/091* (2006.01)

(52) U.S. Cl.
CPC ........ *A61M 16/0051* (2013.01); *A61M 16/00* (2013.01); *A61M 16/0003* (2014.02);
(Continued)

(58) Field of Classification Search
CPC .......... A61M 16/0051; A61M 16/0069; A61M 16/0003; A61M 16/00; A61M 2205/15;
(Continued)

(56) References Cited

U.S. PATENT DOCUMENTS

| | | | | |
|---|---|---|---|---|
| 5,632,269 A | * | 5/1997 | Zdrojkowski | ..... A61M 16/0051 128/204.21 |
| 5,931,160 A | * | 8/1999 | Gilmore | ................ A61M 16/00 128/204.18 |

(Continued)

FOREIGN PATENT DOCUMENTS

| | | |
|---|---|---|
| EP | 2 368 593 A1 | 9/2011 |
| WO | 97/20592 A1 | 6/1997 |

OTHER PUBLICATIONS

Dräger AG & Co. KGaA: Evita-Serie / Savina—Option Maskenbeatmung NIV, Lübeck. 2010. URL: http://www.draeger.com/media/10/01/74/10017467/niv br_9048988_de.pdf.
Dräger AG & Co. KGaA: SmartCare®/PS—Das automatisierte Weaning Protokoll, Lübeck. 2010. URL: http://www.draeger.com/media/10/06/24/10062434/rsp_SmartCare_PS booklet_9051518_de.pdf [abgerufen am Jul. 11, 2012].

(Continued)

*Primary Examiner* — Todd J Scherbel
*Assistant Examiner* — Victoria Leszczak
(74) *Attorney, Agent, or Firm* — McGlew and Tuttle, P.C.

(57) ABSTRACT

Respiration system for non-invasive positive-pressure respiration, with a pressure source providing respiratory gas, with a control and evaluation unit connected to sensors detecting a leakage volume, spontaneous respiration frequency, tidal volume and the inspiration time. The control and evaluation unit I) checks the leakage volume and reduces the inspiratory pressure assistance proceeding to ii) or triggers an alarm and returns to I), ii) checks the frequency and triggers an alarm and returns to I) or reduces or (Continued)

increases the inspiratory pressure and returns to I) or proceeds to step iii), iii) checks the volume and reduces or increases the inspiratory pressure and returns to I) or leaves the pressure assistance unchanged proceeding to step iv), iv) adjusts the time period of the pressure assistance, depending on the inspiration time, the time period being left unchanged if the inspiration time lies in the predefined inspiration time interval, and returns to I).

2 Claims, 3 Drawing Sheets

(52) U.S. Cl.
CPC ......... *A61M 16/0069* (2014.02); *A61B 5/091* (2013.01); *A61M 2016/0036* (2013.01); *A61M 2016/0039* (2013.01); *A61M 2205/15* (2013.01); *A61M 2205/18* (2013.01); *A61M 2205/3303* (2013.01); *A61M 2230/42* (2013.01)

(58) Field of Classification Search
CPC ...... A61M 2205/3303; A61M 2230/42; A61M 2016/0039; A61M 2205/18; A61M 2016/0036; A61B 5/091
See application file for complete search history.

(56) References Cited

U.S. PATENT DOCUMENTS

| | | | | | |
|---|---|---|---|---|---|
| 6,956,572 | B2* | 10/2005 | Zaleski | ................ | A61B 5/0002 345/440.2 |
| 2001/0004893 | A1* | 6/2001 | Biondi | .................. | A61M 16/00 128/204.18 |
| 2003/0037786 | A1* | 2/2003 | Biondi | .................. | A61M 16/00 128/204.21 |
| 2008/0295837 | A1* | 12/2008 | McCormick | ...... | A61M 16/0051 128/204.21 |
| 2014/0034054 | A1* | 2/2014 | Angelico | .......... | A61M 16/0051 128/204.23 |

OTHER PUBLICATIONS

Dräger AG & Co. KGaA: Wegweisende Beatmungstechnologie—Dräger Evita Infinity® V500, Lübeck. 2010. URL: http://www.draeger.com/media/10/03/08/10030806/rsp_evita_infinity_v500 br_9066350_de.pdf [abgerufen am Jul. 11, 2012].

Battisti, Anne, et al. Automatic adjustment of pressure support by a computer-driven knowledge-based system during noninvasive ventilation: a feasibility study. Intensive care medicine, 2006, 32. Jg., Nr. 10, S. 1523-1528.

\* cited by examiner

RESPIRATION SYSTEM

CROSS REFERENCE TO RELATED APPLICATIONS

This application is a United States National Phase Application of International Application PCT/EP2013/051666 filed Jan. 29, 2013 and claims the benefit of priority under 35 U.S.C. §119 of German Patent Application DE 10 2012 003 115.7 filed Feb. 16, 2012, the entire contents of which are incorporated herein by reference.

FIELD OF THE INVENTION

The invention pertains to a respiration system for non-invasive positive-pressure respiration with a pressure source for providing respiratory gas with controllable pressure, which is controlled by a control and analyzing unit, and with sensors connected with the control and analyzing unit, which make it possible to detect the leakage volume, the spontaneous respiration rate, the tidal volume and the inspiration time.

BACKGROUND OF THE INVENTION

Non-invasive ventilation (NIV) denotes a mechanical respiration assistance or form of respiration in which the patient's airways are accessed via a tightly fitting nasal or face mask (non-invasively) rather than via an endotracheal or tracheostomy tube (invasively). A distinction is made in non-invasive respiration therapy between negative-pressure ventilation (NPV) and positive-pressure ventilation (NIPPV—non-invasive positive-pressure ventilation) with the BIPAP (biphasic positive airway pressure) as well as CPAP/ASB (continuous positive airway pressure/assisted spontaneous breathing) respiration patterns. The present invention pertains to NIPPV in CPAP/ASB.

Non-invasive ventilation is used for the therapy of many different forms of respiratory failure and has found acceptance as an addition to conventional, i.e., invasive weaning from the respirator. The CPAP/ASB form of respiration with NIV is thus used to regulate oxygenation and ventilation disorders.

The use of NIV is recommended especially when patients are extubated after a preceding conventional weaning and nevertheless display a significant hypercapnic respiratory failure. It was possible with NIV in these cases both to reduce the respiration time and to reduce the rate of re-intubations, which increase mortality.

General Advantages of NIV Respiration are:
The patient tolerates the respiration better.
No or only slight sedation is necessary.
The patient can communicate/it is possible to communicate with the patient.
Oral feeding is possible.
The breathing air is humidified in a physiologically adequate manner.
The patient can be better mobilized (e.g., while sitting).
Advantages of NIV Over Invasive Respiration:
Shorter respiration time.
Shorter stay in the intensive care unit.
Fewer nosocomial infections, especially pneumonia, especially due to re-intubations.
Lower mortality.
Low cost of therapy.
Prerequisites and Indications for NIV:
The patient must be alert and cooperative.
Respiratory drive as well as swallowing and protective reflexes must be present.
Hemodynamic stability.
Pulmonary indications:
  Chronic respiratory failure
    COPD
    Obstructive sleep apnea
    Disturbances in respiratory drive
    Neuromuscular disorders
  Acute respiratory failure
    Acute COPD
    Pneumonia
    Pulmonary embolism
    Weaning
  Cardiac indications
    Cardiogenic pulmonary edema.

The SmartCare/PS respiration option available for the Dräger EvitaXL and Dräger Evita Infinity V500 respirators offers an automated weaning strategy for the CPAP/ASB invasive form of respiration. According to a clinical guideline, the inspiratory pressure assistance (ASB) on the respirator is sought to be minimized gradually and at short time intervals in order to ultimately accompany the patient autonomously until the patient is able to be extubated over an attempt at spontaneous breathing over 1 to 3 hours. Measured data are sent to the knowledge-based system from the respirator every 5 seconds (spontaneous respiration rate, tidal volume, end-tidal carbon dioxide), and the respiration therapy is automatically adjusted with these measured data every 2 to 5 minutes conform with the clinical guidelines and adequately for the patient's status. It was possible to show in a multicenter randomized study that the respiration time can be reduced by 33% and the weaning time by up to 50% with this automatic respiration adjustment.

The above-described SmartCare/PS adjustment method cannot be used directly for non-invasive respiration with the goal of post-extubation respiratory stabilization. The essential reasons for this are:
Unlike in SmartCare/PS, active weaning is not the therapeutic goal in NIV.
Contrary to SmartCare/PS, active attempt at spontaneous breathing is not desired in NIV.
The $CO_2$ measurement under NIV is fragile and can therefore be used only conditionally, whereas the end-tidal $CO_2$ value is an essential input parameter for SmartCare/PS.
Further respiration parameters must be adjusted, besides the ASB.
In particular, patient-device asynchronies cannot be purposefully avoided with the prior-art method. Leakages, which may be considerable precisely under NIV, are not taken into account in SmartCare/PS. Finally, it is necessary in non-invasive respiration to check the settings more frequently.

SUMMARY OF THE INVENTION

An object of the present invention is to design a respiration system for non-invasive respiration with the CPAP/ASB respiration pattern such that post-extubation respiratory stabilization of the patient is carried out automatically.

Provisions are made according to the present invention for a control and analyzing unit of the respiration system to be set up to check input variables in a certain sequence to determine whether certain criteria are met and to possibly perform an adjustment of the respiration parameters depending on the result of the checking. It was found in connection with the present invention that the following parameters should be checked gradually as input variables:
  Leakage volume (MV_LEAK)
  Spontaneous respiration rate (F_SPON)
  Tidal volume (VT)
  Inspiration time (TI_SPON).

The inspiratory pressure assistance (P-ASB) and the time period during which the inspiratory pressure assistance is carried out are set as output variables. It was found that it is precisely the sequence defined according to the invention and the checking of the criteria indicated that lead to a stable, automated guidance of the respiration system.

Accordingly, the leakage volume must first be checked to determine whether it is above a preset limit value. If it is, the spontaneous respiration rate is checked to determine whether it is within a preset spontaneous respiration rate range, and the tidal volume is checked to determine whether it is within a preset tidal volume range, and if the above-mentioned two conditions are not met, an alarm is triggered, and the process returns to the starting point. Otherwise, if the leakage volume is above the preset leakage volume limit value and the spontaneous respiration rate is within the preset spontaneous respiration rate range and the tidal volume is within the preset tidal volume range, the inspiratory pressure assistance, i.e., the pressure that is provided by the respiration drive, is reduced until the resulting leakage volume drops below the preset limit value.

If this could be done, a check is performed to determine whether the spontaneous respiration rate is above a preset maximum, or below a preset minimum, and if yes, an alarm is triggered and the process returns to the preceding step. The spontaneous respiration rate is subsequently compared with the preset spontaneous respiration frequency range and it is determined whether the spontaneous respiration rate is below, within or above the preset spontaneous respiration rate range. If the spontaneous respiration rate is above the preset spontaneous respiration rate range, the inspiratory pressure assistance is reduced. If the spontaneous respiration rate is below the preset range, the inspiratory pressure assistance is increased. If the inspiratory pressure assistance has been increased or reduced here, the process returns to the first step with the checking of the leakage volume. The inspiratory pressure assistance is left unchanged and the process proceeds to the next step of checking only if the spontaneous respiration rate is within the preset spontaneous respiration rate range.

Next, the tidal volume is checked to determine whether it is below, within or above the preset tidal volume range. If the tidal volume is above the preset tidal volume range, the inspiratory pressure assistance is reduced. If the tidal volume is below the preset tidal volume range, the inspiratory pressure assistance is increased. When the inspiratory pressure assistance has now been increased or reduced, the process returns to the first step with the checking of the leakage volume. The inspiratory pressure assistance is left unchanged and the process proceeds to the next step of checking only if the current tidal volume is in the preset tidal volume range.

Finally, the time or time period within which the inspiratory pressure assistance is carried out during a breath is set as a function of the patient's inspiration time. The time period of pressure assistance can be set, for example, by a criterion of the parameter % PIF, where PIF denotes "peak inspiration flow." A time period of 5% PIF means now that the inspiratory pressure assistance is ended when the volume flow is reduced to 5% compared to its peak value during the respective breath. It is correspondingly also possible to set a shorter inspiratory pressure assistance in relation to the duration of the breath, for example, 70% PIF, which means that the inspiratory pressure assistance is ended already when the volume flow has dropped to 70% of its peak value during this breath.

The present invention will be described below on the basis of an exemplary embodiment shown in the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
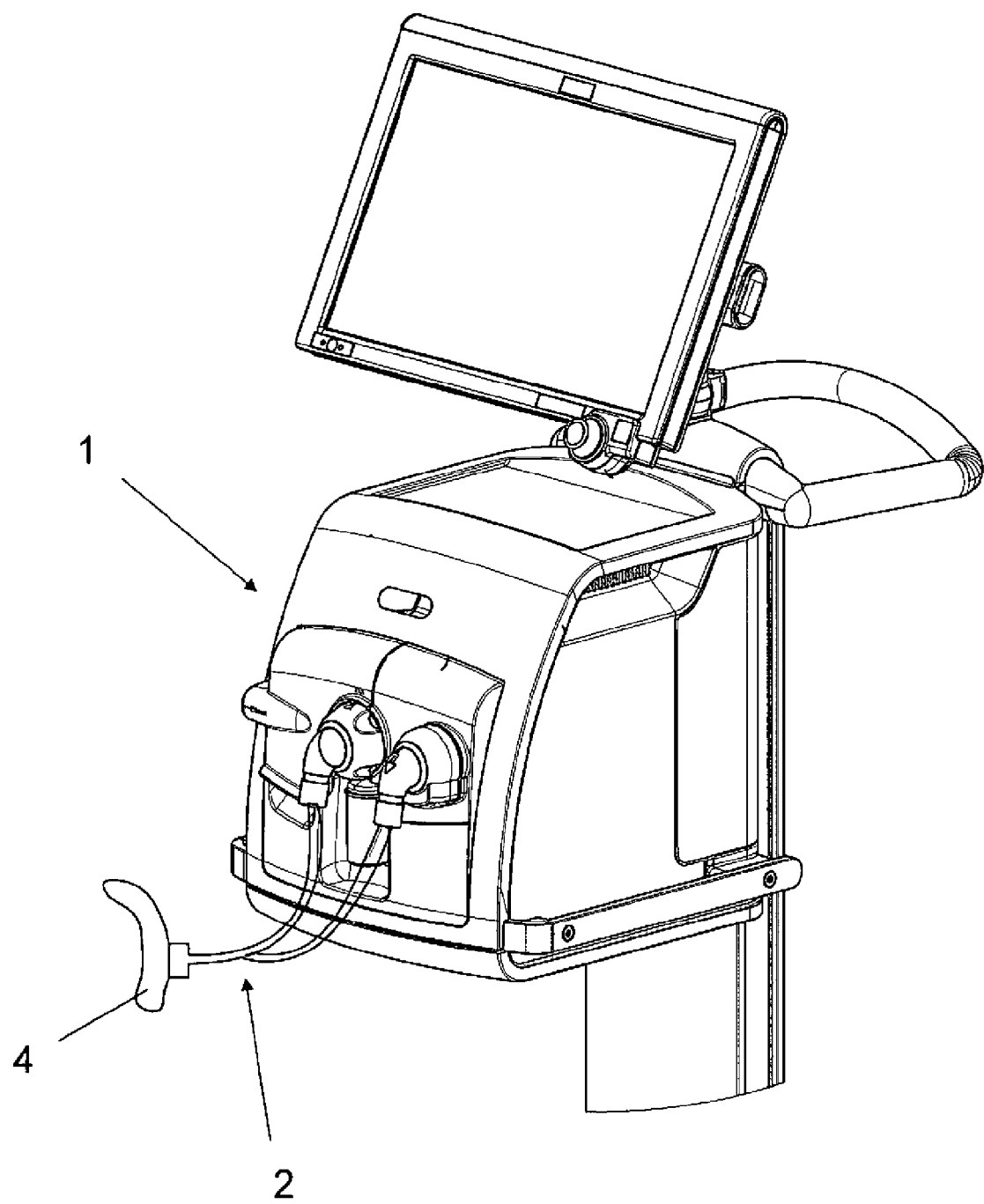
FIG. 1 is a perspective view of a respiration system.

Referring to the drawings in particular, FIG. 1 shows a respiration system 1 with a tube system 2, which comprises an inspiratory line and an expiratory line, which open into a Y-piece at a breathing mask 4. A pressure source and a control and analyzing unit, which controls the output of respiratory gas with the desired pressure curve from the pressure source, are accommodated within the respiration system. Furthermore, sensors for detecting pneumatic variables, which are not shown specifically in FIG. 1, are present in the usual manner. The leakage volume, spontaneous respiration rate, tidal volume and further parameters are detected in the usual manner by the sensors.

Figure 2:
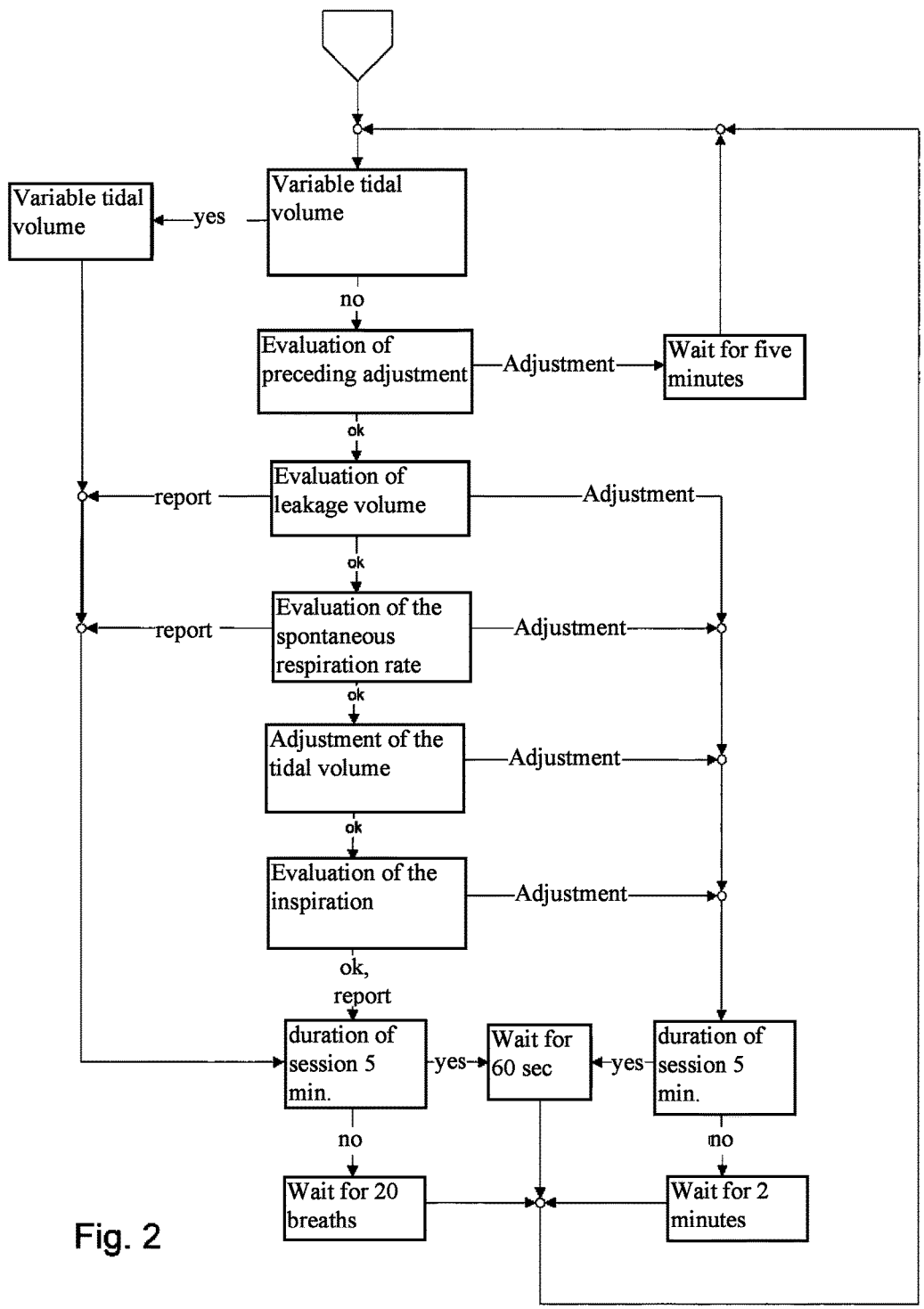
FIG. 2 is a flow chart of the control of the respiration system according to the present invention.

With reference to FIG. 2, the control and analyzing unit checks at first whether the tidal volume is variable. If not, the previous adjustment is evaluated. If the inspiratory pressure assistance was increased before, it is checked whether the patient's spontaneous respiration rate could be reduced hereby. If yes, one proceeds to the next step of checking.

If neither the patient's spontaneous respiration rate could be reduced nor could the tidal volume be increased by the preceding increase in the inspiratory pressure assistance, the preceding increase in the inspiratory pressure assistance is taken back and one waits 5 minutes until the next cycle.

If the patient's spontaneous respiration rate could not be reduced by the preceding increase in the inspiratory pressure assistance, but the tidal volume has increased, one proceeds to the next step of checking if the tidal volume is not above the preset tidal volume range. Should the tidal volume be above the preset tidal volume range, no further adjustments are made at first and one waits 5 minutes until the next cycle.

At the beginning of the automated setting of the respiration system, the user provides the system information on the patient: Body height as well as ranges in which the leakage volume, spontaneous respiration rate and tidal volume are allowed to vary. Within the first 5 minutes after the start of the respiration system, a rating is performed every 60 seconds from the input values P_ASB, PIF, VT, F-SPON, TI-SPON and MV_LEAK, which can lead to an autonomous adjustment of the set variables P_ASB and/or PIF. The evaluation is repeated and/or an adjustment is performed every 20 breaths after the first 5 minutes, and one waits for 2 minutes each after an autonomous adjustment.

Figure 3:
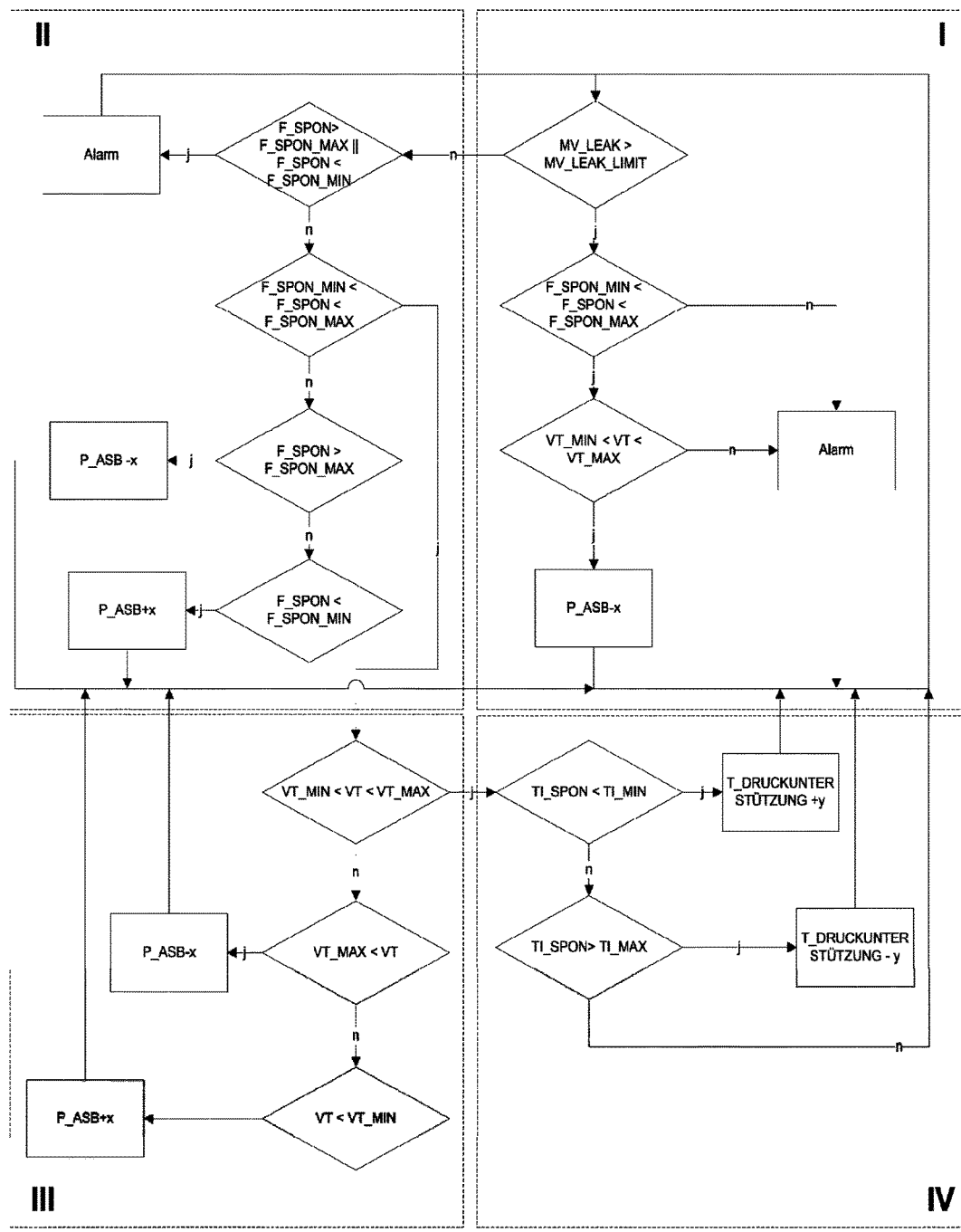
FIG. 3 is a flow chart of the sequences of polling steps in a respiration system according to the present invention.

The higher-level, cyclically recurring testing procedure can be described as follows: After checking the current tidal volume to determine whether it exceeds the range and after retrospective assessment of the previous autonomous parameter adjustment (assess prior adjustment) and corresponding correction, stabilization is started automatically in four steps based on a fixed, preset assessment sequence, and these step sequences are visualized in the flow chart in FIG. 3, where the blocks designated by I through IV correspond to the following steps 1 through 4 and to the steps I) through iv) according to the invention:

1. Analysis of the existing leakage volume MV_LEAK and, if the leakage volume exceeds a limit value, checking to determine whether the spontaneous respiration rate F-SPON is within a preset spontaneous respiration rate range and whether the tidal volume CT is within a preset tidal volume range. If one or both of the latter two conditions are not met, an alarm is triggered and the process returns to the starting point. Otherwise, and if the leakage volume is above the limit value, the inspiratory pressure assistance P_ASB is reduced (which is indicated by P_ASB-x in FIG. 3) in order to reduce the leakage volume, and the process returns to the starting point; if the leakage volume is below the limit value, the process is continued with the following step 2 (this step is designated by "evaluation of the leakage volume" in FIG. 2);

2. If the spontaneous respiration rate F_SPON is above a preset maximum or below a preset minimum, an alarm is triggered and the process returns to step 1; otherwise, the spontaneous respiration rate F-SPON is compared with the preset spontaneous respiration rate range, which is within the range between the maximum and the minimum, and if the spontaneous respiration rate F_SPON is above the preset spontaneous respiration rate range, the inspiratory pressure assistance is reduced (indicated by P_ASB-x), and if the spontaneous respiration rate is below the preset range, the inspiratory pressure assistance is increased (P_ASB+x); after an increase or reduction of the inspiratory pressure assistance, the process returns to step 1, and if the spontaneous respiration rate F-SPON is in the preset spontaneous respiration rate range, the inspiratory pressure assistance is left unchanged and the process proceeds to step 3 (this step is designated by "evaluation of the spontaneous respiration rate" in FIG. 2).

3. The inspiratory pressure assistance P-ASB is adjusted or is not adjusted depending on the tidal volume VT, namely, P-ASB is reduced (P-ASB-x) if the tidal volume VT is above the reset tidal volume range, or P_ASB is increased (P_ASB+x) if the tidal volume VT is below the preset tidal volume range. The process returns again to step 1 after an increase or reduction thus triggered. P_ASB is left unchanged and the process proceeds to step 4 (this step is designated by "evaluation of the tidal volume" in FIG. 2) only if the tidal volume VT is in the preset tidal volume range.

4. The time period during which the inspiratory pressure assistance is carried out during one breath is set as a function of the inspiration time by increasing the time period of the inspiratory pressure assistance (T_DRUCK-UNTERSTÜTZUNG+y) if the inspiration time TI_SPON is below a preset inspiration time range, and by reducing it (T_DRUCKUNTERSTÜTZUNG-y) if the inspiration time is above the preset inspiration range, and it is left unchanged if the inspiration time is in the preset inspiration time range, and the process returns to step 1 (this step is designated by evaluation of the inspiration time" in FIG. 2).

Situations of a respiration process are listed below in a table with values for the leakage volume, spontaneous respiration rate, tidal volume and inspiration time, and the corresponding conclusion and the change resulting therefrom in P_ASB and % PIP are shown.

The limit value for the leakage volume equals 15 L/minute in this example. The preset spontaneous respiration rate range is 14-29 bpm (breaths per minute). The preset maximum of the spontaneous respiration rate, above which an alarm is triggered and the process is returned to step 1, equals 40 bpm. The preset minimum, below which an alarm is likewise triggered and the process is returned to the first step, equals 8 bpm.

The preset tidal volume range is 5-10 mL/kg (tidal volume per kg of body weight).

The preset inspiration time range is 0.6-1.2 sec.

| Evaluation of the Leakage Volume | | | |
|---|---|---|---|
| Leakage volume [L/minute] | Diagnosis | Δ PS (mbar) | PIF |
| 0-15 | Adequate assistance | No adjustment | No adjustment |
| 16-30 | Check for leakages | −1 | No adjustment |

| Evaluation of the Spontaneous Respiration Rate | | | |
|---|---|---|---|
| Spontaneous respiration rate [bpm] | Diagnosis | Δ PS [mbar] | PIF |
| >40 | Tachypnea | No adjustment | No adjustment |
| 36-40 | Excessively weak assistance | +3 | No adjustment |
| 33-35 | Excessively weak assistance | +2 | No adjustment |
| 30-32 | Excessively weak assistance | +1 | No adjustment |
| 14-29 | Adequate assistance | No adjustment | No adjustment |
| 11-13 | Excessively great assistance | −2 | No adjustment |
| 8-10 | Excessively great assistance | −3 | No adjustment |
| <8 | Bradypnea | No adjustment | No adjustment |

| Evaluation of the Tidal Volume | | | |
|---|---|---|---|
| Tidal volume per kg [mL/kg] | Diagnosis | Δ PS [mbar] | PIF |
| <5 | Excessively weak assistance | +2 | No adjustment |
| 5-10 | Adequate assistance | No adjustment | No adjustment |
| 11-12 | Excessively great assistance | −2 | No adjustment |
| 13-14 | Excessively great assistance | −3 | No adjustment |
| >14 | Excessively great assistance | −4 | No adjustment |

| Evaluation of the Inspiration Time | | | |
|---|---|---|---|
| Inspiration time [sec] | Diagnosis | Δ PS [mbar] | PIF |
| <0.6 | Excessively brief assistance | No adjustment | 25 |
| 0.6-1.2 | Adequate assistance | No adjustment | No adjustment |
| 1.3-1.7 | Excessively long assistance | No adjustment | 50 |
| >1.7 | Excessively long assistance | No adjustment | 70 |

While specific embodiments of the invention have been shown and described in detail to illustrate the application of the principles of the invention, it will be understood that the invention may be embodied otherwise without departing from such principles.

The invention claimed is:

1. A respiration system for non-invasive positive-pressure ventilation, the respiration system comprising:
   a pressure source for providing respiratory gas with controllable pressure;
   sensors to determine a leakage volume, a spontaneous respiration rate, a tidal volume and an inspiration time;
   a control and analyzing unit configured to control the pressure source connected with the sensors, wherein the control and analyzing unit is configured to automatically perform the following measurements and settings in the sequence indicated:
   i) to check the leakage volume (MV_LEAK) to determine whether the leakage volume is above a preset limit value, and to reduce an inspiratory pressure assistance if the leakage volume (MV_LEAK) is above a preset limit value and if the spontaneous respiration rate (F_SPON) is within a preset spontaneous respiration rate range and the tidal volume (VT) is within a preset tidal volume range, and to trigger an alarm if the spontaneous respiration rate (F_SPON) is outside the preset spontaneous respiration rate range or if the tidal volume (VT) is outside the preset tidal volume range and to return to a starting point, and to proceed to step ii) only if the leakage volume is below the preset limit value;
   ii) to trigger the alarm and to return to step i) if the spontaneous respiration rate (F_SPON) is above a preset maximum or below a preset minimum, and to compare the spontaneous respiration rate (F_SPON) with the preset spontaneous respiration rate range, which is within the range between the preset maximum and the preset minimum, and to reduce the inspiratory pressure assistance if the spontaneous respiration rate (F_SPON) is above the preset spontaneous respiration rate range, and to increase the inspiratory pressure assistance if the spontaneous respiration rate (F_SPON) is below the preset range and to return to step i) after the increase or the reduction of the inspiratory pressure assistance, and to leave the inspiratory pressure assistance unchanged and to proceed to step iii) if the spontaneous respiration rate (F_SPON) is within the preset spontaneous respiration rate range;
   iii) to check the tidal volume (VT) to determine whether the tidal volume is within the preset tidal volume range, and to reduce the inspiratory pressure assistance if the tidal volume is above the preset tidal volume range, and to increase the inspiratory pressure assistance if the tidal volume (VT) is below the preset tidal volume range and to return to step i) after the reduction or the increase, and to leave the inspiratory pressure assistance unchanged and to proceed to step iv) if the tidal volume (VT) is in the preset tidal volume range, and
   iv) to set a time period during which the inspiratory pressure assistance is carried out as a function of the patient's inspiration time by increasing the time period of the inspiratory pressure assistance if the inspiration time (TI_SPON) is below a preset inspiration time range, and reducing the time period of the inspiratory pressure assistance if the inspiration time (TI_SPON) is above the preset inspiration time range, while the time period of the inspiratory pressure assistance is left unchanged if the inspiration time is within the preset inspiration time range, and the process is returned to step i).

2. A non-invasive positive-pressure ventilation method comprising the steps of:
   providing respiration system comprising:
   a pressure source for providing respiratory gas with controllable pressure;
   sensors to determine a leakage volume, a spontaneous respiration rate, a tidal volume and an inspiration time;
   a control and analyzing unit configured to control the pressure source connected with the sensors, wherein the control and analyzing unit is configured to automatically perform the following measurements and settings in the sequence indicated:
   i) to check the leakage volume (MV_LEAK) to determine whether the leakage volume (MV_LEAK) is above a preset limit value, and to reduce the inspiratory pressure assistance if the leakage volume is above the preset limit value and if the spontaneous respiration rate (F_SPON) is within a preset spontaneous respiration rate range and the tidal volume (VT) is within a preset tidal volume range, and to trigger an alarm if the spontaneous respiration rate (F_SPON) is outside the preset spontaneous respiration rate range or if the tidal volume (VT) is outside the preset tidal volume range and to return to a starting point, and to proceed to step ii) only if the leakage volume is below the preset limit value;
   ii) to trigger the alarm and to return to step i) if the spontaneous respiration rate (F_SPON) is above a preset maximum or below a preset minimum, and to compare the spontaneous respiration rate (F_SPON) with the preset spontaneous respiration rate range, which is within the range between the preset maximum and the preset minimum, and to reduce the inspiratory pressure assistance if the spontaneous respiration rate (F_SPON) is above the preset spontaneous respiration rate range, and to increase the inspiratory pressure assistance if the spontaneous respiration rate (F_SPON) is below the preset range and to return to step i) after the increase or the reduction of the inspiratory pressure assistance, and to leave the inspiratory pressure assistance unchanged and to proceed to step iii) if the spontaneous respiration rate (F_SPON) is within the preset spontaneous respiration rate range;
   iii) to check the tidal volume (VT) to determine whether the tidal volume is within the preset tidal volume range, and to reduce the inspiratory pressure assistance if the tidal volume is above the preset tidal volume range, and to increase the inspiratory pressure assistance if the tidal volume (VT) is below the preset tidal volume range and to return to step i) after the reduction or the increase, and to leave the inspiratory pressure assistance unchanged and to proceed to step iv) if the tidal volume (VT) is in the preset tidal volume range, and
   iv) to set a time period during which the inspiratory pressure assistance is carried out as a function of the patient's inspiration time by increasing the time period of the inspiratory pressure assistance if the inspiration time (TI_SPON) is below a preset inspiration time range, and reducing the time period of the inspiratory pressure assistance if the inspiration time (TI_SPON) is above the preset inspiration time range, while the time period of the inspiratory pressure assistance is left unchanged if the inspiration time is within the preset inspiration time range, and the process is returned to step i).

* * * * *